United States Patent
Leach et al.

(10) Patent No.: US 9,815,038 B2
(45) Date of Patent: Nov. 14, 2017

(54) METHOD AND APPARATUS TO CREATE AUTOLOGOUS CLOTTING SERUM

(71) Applicant: Biomet Biologics, LLC, Warsaw, IN (US)

(72) Inventors: Michael D. Leach, Warsaw, IN (US); Jennifer E. Woodell-May, Warsaw, IN (US); Hillary Overholser, Warsaw, IN (US); Joel C. Higgins, Claypool, IN (US); Jason Chavarria, Warsaw, IN (US); Ned M. Hamman, Leesburg, IN (US)

(73) Assignee: Biomet Biologics, LLC, Warsaw, IN (US)

( * ) Notice: Subject to any disclaimer, the term of this patent is extended or adjusted under 35 U.S.C. 154(b) by 485 days.

(21) Appl. No.: 14/081,121

(22) Filed: Nov. 15, 2013

(65) Prior Publication Data

US 2014/0071787 A1   Mar. 13, 2014

Related U.S. Application Data

(62) Division of application No. 13/209,982, filed on Aug. 15, 2011, now Pat. No. 8,586,324.

(51) Int. Cl.
*A01B 1/00* (2006.01)
*B01F 1/00* (2006.01)
(Continued)

(52) U.S. Cl.
CPC .......... *B01F 15/026* (2013.01); *B01F 1/0027* (2013.01); *B01F 3/04446* (2013.01);
(Continued)

(58) Field of Classification Search
CPC  B01F 15/026; B01F 15/0227; B01F 15/0266; A61K 35/16
See application file for complete search history.

(56) References Cited

U.S. PATENT DOCUMENTS

| | | |
|---|---|---|
| 5,139,031 A | 8/1992 | Guirguis |
| 5,733,545 A | 3/1998 | Hood, III |

(Continued)

FOREIGN PATENT DOCUMENTS

WO   WO-0074713 A1   12/2000

OTHER PUBLICATIONS

"U.S. Appl. No. 13/209,982, Examiner Interview Summary dated Feb. 4, 2013", 3 pgs.
(Continued)

*Primary Examiner* — Nathan Bowers
(74) *Attorney, Agent, or Firm* — Schwegman Lundberg & Woessner, P.A.

(57) ABSTRACT

A clotting serum production device including a main chamber, an inlet housing, and an outlet port. The main chamber is defined by a first end wall, a second end wall opposite to the first end wall, and a side wall extending between the first end wall and the second end wall. The inlet housing extends from the first end wall. The inlet housing includes a first inlet port, a second inlet port, and a first conduit extending between the first inlet port and a second conduit. The second conduit extends between the second inlet port and the main chamber. The inlet housing is configured to provide one-way fluid flow from the first inlet port to the second inlet port and to provide one-way fluid flow from the second inlet port to the main chamber. An outlet port is in fluid communication with the main chamber and provides fluid communication with an exterior of the clotting serum production device.

20 Claims, 8 Drawing Sheets

(51) Int. Cl.
  *A61K 35/00* (2006.01)
  *B01F 15/02* (2006.01)
  *B01F 13/00* (2006.01)
  *B01F 15/00* (2006.01)
  *B01F 3/04* (2006.01)
  *A61K 35/16* (2015.01)

(52) U.S. Cl.
  CPC ...... *B01F 13/0023* (2013.01); *B01F 13/0052* (2013.01); *B01F 15/00512* (2013.01); *B01F 15/0227* (2013.01); *B01F 15/0237* (2013.01); *B01F 15/0266* (2013.01); *A61K 35/16* (2013.01)

(56) References Cited

U.S. PATENT DOCUMENTS

| | | | |
|---|---|---|---|
| 5,887,755 | A | 3/1999 | Hood, III |
| 5,985,315 | A | 11/1999 | Patat et al. |
| 6,274,090 | B1 | 8/2001 | Coelho et al. |
| 6,444,228 | B1 | 9/2002 | Baugh et al. |
| 6,472,162 | B1 | 10/2002 | Coelho et al. |
| 6,830,762 | B2 | 12/2004 | Baugh et al. |
| 6,899,813 | B2 | 5/2005 | Dolecek et al. |
| 6,905,612 | B2 | 6/2005 | Dorian et al. |
| 6,936,033 | B2 | 8/2005 | McIntosh et al. |
| 7,056,722 | B1 | 6/2006 | Coelho et al. |
| 7,309,428 | B2 * | 12/2007 | Tsai ............ B01D 61/18 210/198.1 |
| 7,604,626 | B2 | 10/2009 | McIntosh et al. |
| 7,694,828 | B2 | 4/2010 | Swift et al. |
| 7,708,152 | B2 | 5/2010 | Dorian et al. |
| 8,586,324 | B2 | 11/2013 | Leach et al. |
| 9,107,668 | B2 * | 8/2015 | Melsheimer ..... A61B 17/12022 |
| 2004/0120942 | A1 | 6/2004 | McGinnis et al. |
| 2005/0129674 | A1 | 6/2005 | Baugh et al. |
| 2005/0170006 | A1 | 8/2005 | Baugh et al. |
| 2005/0252867 | A1 | 11/2005 | Baugh et al. |
| 2006/0034935 | A1 | 2/2006 | Pronovost et al. |
| 2006/0140923 | A1 | 6/2006 | Evangelista et al. |
| 2008/0044852 | A1 | 2/2008 | Kanayinkal et al. |
| 2009/0306623 | A1 | 12/2009 | McIntosh et al. |
| 2012/0027746 | A1 | 2/2012 | Dorian et al. |
| 2013/0045523 | A1 | 2/2013 | Leach et al. |

OTHER PUBLICATIONS

"U.S. Appl. No. 13/209,982, Non Final Office Action dated Nov. 6, 2012", 7 pgs.
"U.S. Appl. No. 13/209,982, Notice of Allowance dated Mar. 5, 2013", 5 pgs.
"U.S. Appl. No. 13/209,982, Notice of Allowance dated Jul. 17, 2013", 6 pgs.
"U.S. Appl. No. 13/209,982, Response filed Feb. 5, 2013 to Non Final Office Action dated Nov. 6, 2012", 17 pgs.
"U.S. Appl. No. 13/209,982, Response filed Sep. 24, 2012 to Restriction Requirement dated Aug. 22, 2012", 13 pgs.
"U.S. Appl. No. 13/209,982, Restriction Requirement dated Aug. 22, 2012", 5 pgs.
"Clotalyst® Autologous Clotting Factor" brochure. (Aug. 15, 2008) Biomet Biologics.
"Clotalyst® Autologous Serum Collection System" brochure. (May 31, 2010) Biomet Biologics.
"MarrowStim™ Concentration System," brochure. (Jun. 15, 2008) Biomet Biologics.
Kumar, Vijay et al., "Autologous Thrombin: Intraoperative Production From Whole Blood." Journal of American Society of Extra-Corporeal Technology. JECT: (Apr. 2008); 40:94-98.
Semple, E. et al. "Quality of Thrombin Produced from the Patient's Own Plasma Using the TPD, a New Thrombin-Processing Device" Journal of American Society of Extra-Corporeal Technology, vol. 37, pp. 196-200 (Jun. 2005).

* cited by examiner

METHOD AND APPARATUS TO CREATE AUTOLOGOUS CLOTTING SERUM

CROSS-REFERENCE TO RELATED APPLICATIONS

This application is a divisional of U.S. patent application Ser. No. 13/209,982 filed Aug. 15, 2011. The entire disclosure of the above application is incorporated herein by reference.

FIELD

The present disclosure relates to methods and devices for preparing and isolating clotting serum.

BACKGROUND

This section provides background information related to the present disclosure and is not necessarily prior art.

Clotting serum (including thrombin and various clotting factors) prepared from whole blood, plasma, bone marrow aspirate, or any other suitable source, can be used to enhance clotting of, for example, blood, platelet rich plasma, platelet poor plasma, concentrated platelet poor plasma, and bone marrow aspirate. The present teachings include methods and devices for preparing and isolating clotting serum.

SUMMARY

This section provides a general summary of the disclosure, and is not a comprehensive disclosure of its full scope or all of its features.

The present teachings provide for a clotting serum production device including a main chamber, an inlet housing, and an outlet port. The main chamber is defined by a first end wall, a second end wall opposite to the first end wall, and a side wall extending between the first end wall and the second end wall. The inlet housing extends from the first end wall. The inlet housing includes a first inlet port, a second inlet port, and a first conduit extending between the first inlet port and a second conduit. The second conduit extends between the second inlet port and the main chamber. The inlet housing is configured to provide one-way fluid flow from the first inlet port to the second inlet port and to provide one-way fluid flow from the second inlet port to the main chamber. An outlet port is in fluid communication with the main chamber and provides fluid communication with an exterior of the clotting serum production device.

The present teachings further provide for a mixing chamber for a clotting serum production device. The mixing chamber includes a housing, a first inlet port, a first outlet port, a solid calcium salt, and a filter. The housing defines a reservoir. The first inlet port is at a first end of the housing. The first outlet port is at a second end of the housing. The second end of the housing is opposite to the first end of the housing. The solid calcium salt is included in the reservoir. The filter is mounted within the reservoir between the first outlet port and the solid calcium salt.

The present teachings further provide for a method for preparing and isolating clotting serum. The method includes the following: adding a reagent and a clotting serum source to a reaction chamber of a clotting serum production device that includes an activator; mixing the reagent, clotting serum source, and the activator by shaking to bring contents of the clotting serum production device to a foam; after mixing, one of placing the device in a vacuum, or at room temperature and standard atmosphere for a predetermined period of time; and extracting clotting serum released by the clotting serum source from the reaction chamber Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
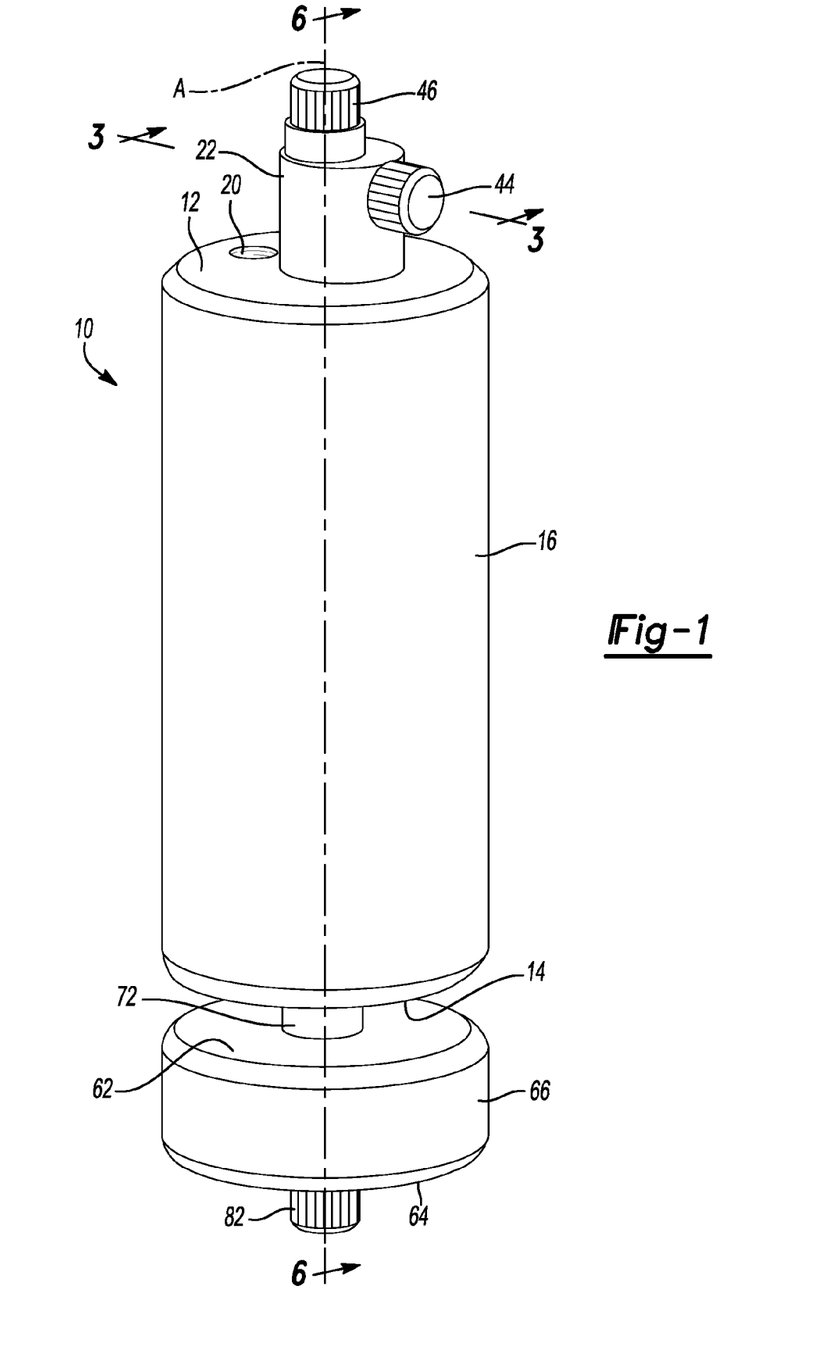
FIG. 1 is a perspective view of a clotting serum preparation and isolation device according to the present teachings.
Figure 2:
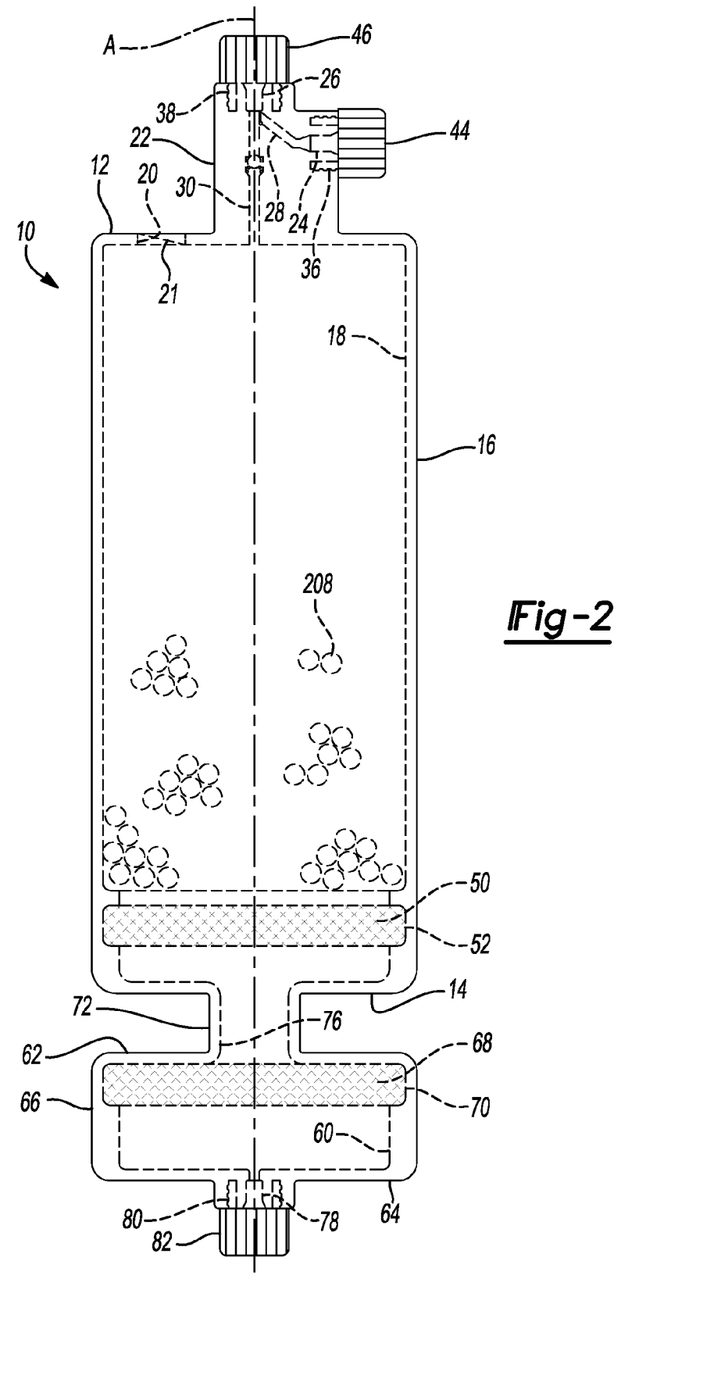
FIG. 2 is a side view of the device of FIG. 1 with internal features illustrated in phantom.

With initial reference to FIGS. 1 and 2, a preparation device for preparing and isolating clotting serum is illustrated at reference numeral 10. The preparation device 10 generally includes a first end wall 12, a second end wall 14, and a side wall 16. The first end wall 12 is opposite to the second end wall 14. The side wall 16 is between the first end wall 12 and the second end wall 14 and extends from the first end wall 12 to the second end wall 14. The first end wall 12, the second end wall 14, and the side wall 16 define a main chamber 18. The side wall 16 is cylindrical and defines the main chamber 18 as cylindrical. A longitudinal axis A extends through an axial center of the main chamber 18. The side wall 16 can have any suitable cross-sectional shape or configuration to define the main chamber 18 with any suitable shape or configuration. For example, the side wall 16 can have a plurality of planar surfaces, such as four, to define the main chamber 18 as having a square or rectangular shape.

The preparation device 10 further includes a vacuum port 20 having a one-way valve 21. The vacuum port 20 is an opening defined by the first end wall 12. The one-way valve 21 is positioned in the opening. The one-way valve 21 permits passage of air out from within, but not into, the main chamber 18 when the preparation device 10 is placed in a vacuum. The one-way valve 21 restricts passage of clotting serum and other materials in either direction. The one-way valve 21 can be any suitable device, configuration, or feature that permits air to flow out from within, but not into, the main chamber 18. The vacuum port 20 can be at any other suitable location of the main chamber 18. For example, the vacuum port 20 can be defined by the second end wall 14 or the side wall 16.

The preparation device 10 also includes inlet housing 22, which is at the first end wall 12. The inlet housing 22 can be integral with the first end wall 12 or modular. With additional reference to FIGS. 2 and 3, the inlet housing 22 generally includes and defines a first inlet port 24, a second inlet port 26, a first conduit 28, a second conduit 30, a first valve or inlet valve 32, and a second valve 34. In addition to being at the first end wall 12, the inlet housing 22 can be at any other suitable position on the device, such as at the side wall 16.

Figure 3:
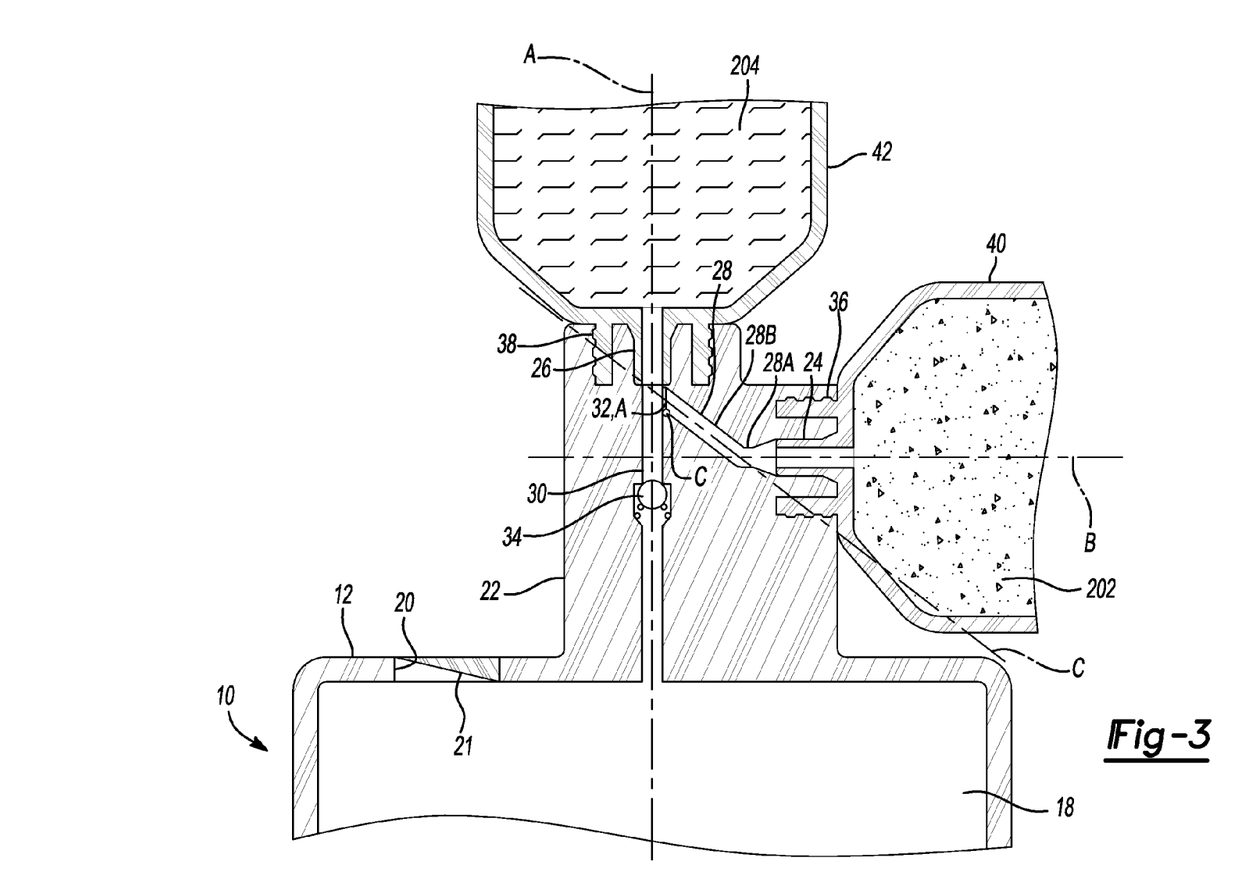
FIG. 3 is a cross-sectional view of an inlet housing of the device of FIG. 1 through line 3-3 of FIG. 1 with first and second syringes connected thereto.

The first inlet port 24 and the second inlet port 26 are each openings defined by the inlet housing 22 at an exterior of the inlet housing 22, and are positioned such that the first longitudinal axis A extends through the first inlet port 24 and a second axis B extends through the second inlet port 24. The second axis B is transverse and perpendicular to the first longitudinal axis A. Thus, the first inlet port 24 and the second inlet port 26 are orientated about 90° with respect to one another. The first inlet port 24 is in fluid communication with the first conduit 28 and the second inlet port 26 is in fluid communication with the second conduit 30. The first conduit 28 and the second conduit 30 can each be passages defined in the housing or separate members, such as hoses.

Figure 4:
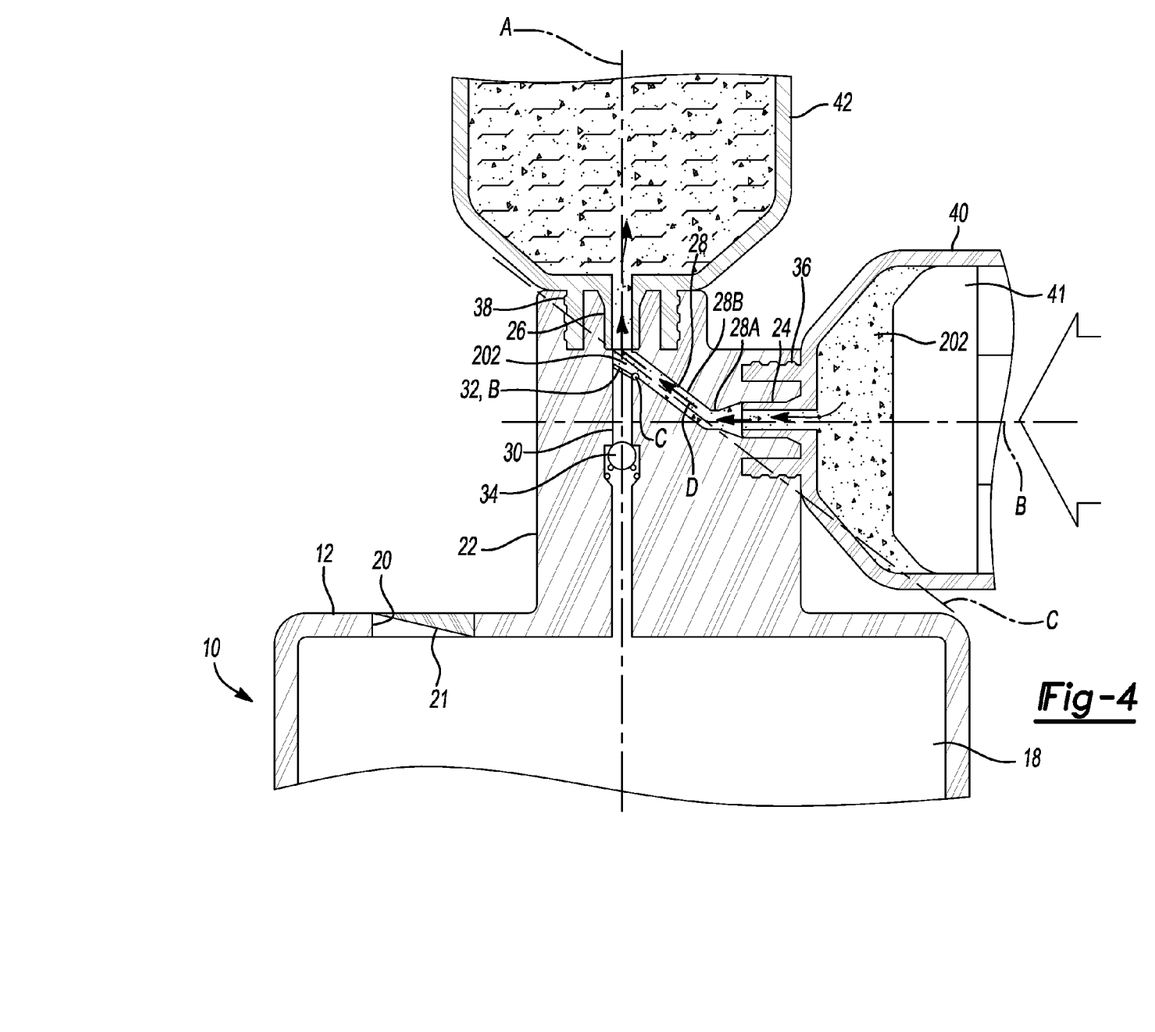
FIG. 4 is similar to FIG. 3 and illustrates material being transferred between the first syringe and the second syringe through the inlet housing along a first fluid flow path.
Figure 5:
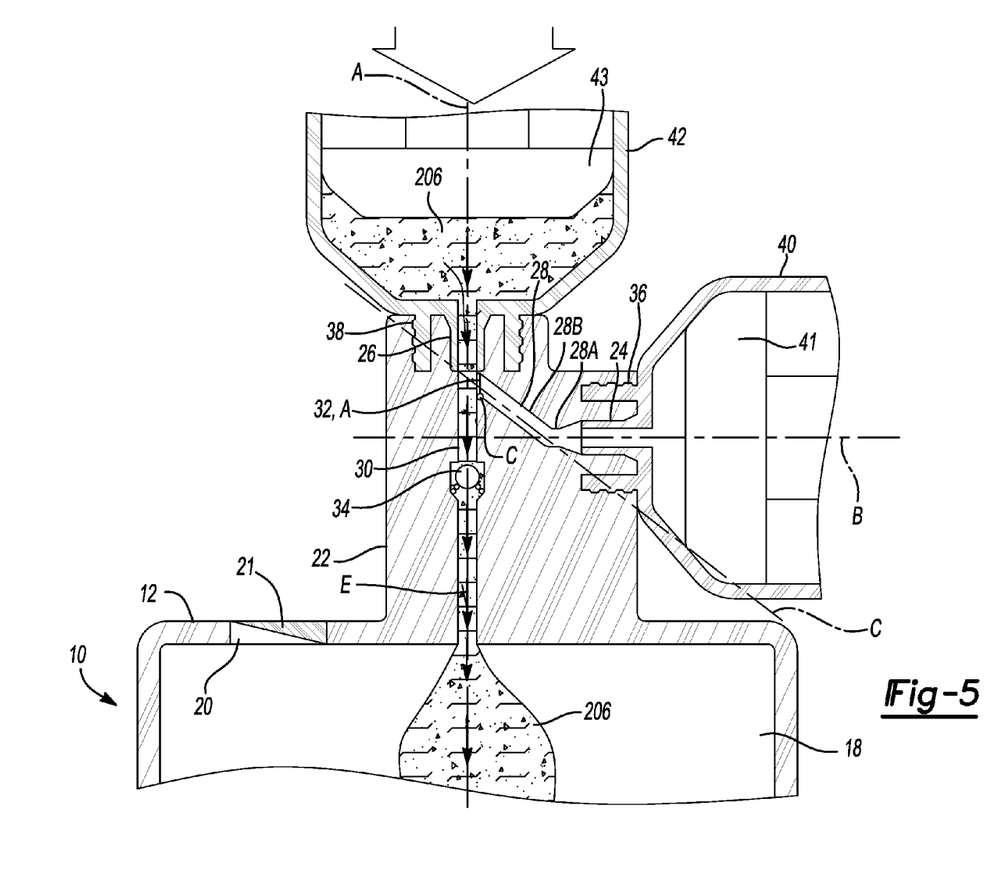
FIG. 5 is similar to FIG. 3 and illustrates material being transferred from the second syringe to a main chamber of the device through the inlet housing along a second fluid flow path.

A first connector 36 is at the first inlet port 24 and a second connector 38 is at the second inlet port 26. The first connector 36 and the second connector 38 can be any suitable coupling devices or features configured to connect suitable delivery devices, such as syringes, to the first inlet port 24 and the second inlet port 26 respectively. For example, the first connector 36 and the second connector 38 can each be luer locks configured to respectively connect a first syringe 40 to the first inlet port 24 and a second syringe 42 to the second inlet port 26, as illustrated in FIGS. 3-5. The first connector 36 is concentric with the first inlet port 24 and the second connector 38 is concentric with the second inlet port 26 to facilitate undisrupted flow of material through the first inlet port 24 and the second inlet port 26.

The first conduit 28 and the second conduit 30 are each defined by the inlet housing 22 and are passageways in the inlet housing 22. As discussed previously, the first conduit 28 and the second conduit 30 can also be separate members, such as hoses or pipes. The first conduit 28 extends from the first inlet port 24 to the second conduit 30 and connects with the second conduit 30. The second conduit 30 extends from the second inlet port 26 to the main chamber 18 along the first longitudinal axis A.

The first conduit 28 includes a first portion 28A and a second portion 28B. The first portion 28A is proximate to the first inlet port 24 and the second portion 28B is between the first portion 28A and the second conduit 30. The second axis B, which is perpendicular to the first longitudinal axis A, extends through an axial center of the first portion 28A. A third axis C, which is not perpendicular to either the first longitudinal axis A or the second longitudinal axis B, extends through an axial center of the second portion 28B. The second portion 28B connects with the second conduit 30 such that the third axis C intersects the first longitudinal axis A at an angle that is greater than 90°, as measured between the third axis C and a portion of the first longitudinal axis A proximate to the second inlet port 26. Orientating the second portion 28B of the first conduit 28 at an angle relative to the second conduit 30 facilitates flow of material from the first inlet port 24 to the second inlet port 26 without the material directly passing from the first conduit 28 into the main chamber 18. As a result of the angle at which the first conduit 28 connects with the second conduit 30, fluid flowing through the first conduit 28 is directed toward the second inlet port 26 and away from the main chamber 18.

The first conduit 28 and the second conduit 30 together provide fluid communication between the first inlet port 24 and the second inlet port 26 along a first pathway "D" (FIG. 4), as further described herein. The second conduit 30 provides fluid communication between the second inlet port 26 and the main chamber 18 along a second pathway "E" (FIG. 5), as further described herein. The first and second conduits 28 and 30 can be any suitable device, structure, or feature configured to permit passage of biological material and an activator (further described herein) through the inlet housing 22. For example, the first and second conduits 28 and 30 can be channels defined in the housing, hoses, or pipes.

The first valve 32 is positioned where the first conduit 28 and the second conduit 30 connect to each other. The first valve 32 is a one-way hinge or flap valve moveable between a first position A (FIGS. 3 and 5) and a second position B (FIG. 4) by rotation about a pivot point C. In the first position A, the first valve 32 extends approximately parallel to the first longitudinal axis A. In the second position B, the first valve 32 is rotated from the first position A such that the first valve 32 extends across the first longitudinal axis A and across the second conduit 30 to restrict passage of material through the second conduit 30 and into the main chamber 18. The first valve 32 is biased in the first position A and remains in the first position A unless a force, such as a fluidic force, acts against it.

In the first position A (FIGS. 3 and 5), the first valve 32 extends across and thus blocks the first conduit 28 at the intersection of the first conduit 28 and the second conduit 30. The first valve 32 does not extend within the second conduit 30 when in the first position A. Thus, in the first position A the first valve 32 restricts flow of material from the first conduit 28 to the second conduit 30 and permits flow of material through an entirety of the second conduit 30 from the second inlet port 26 to the main chamber 18 along the second pathway E.

Flow of material through the first conduit 28 from the first syringe 40 contacts the first valve 32 to move the first valve 32 to the second position B. In the second position B (FIG. 4), the first valve 32 extends across and thus blocks the second conduit 30, but does not block the first conduit 28. Thus, in the second position B the first valve 32 permits flow of material from the first conduit 28 to the second conduit 30 and out through the second inlet port 26 along the first pathway D. The first valve 32 restricts flow of material into the main chamber 18 when the first valve 32 is in the second position B. As further described herein, limiting flow of material from the first syringe 40 to only the second syringe 42, and restricting the flow of material into the main chamber 18, allows contents of the first syringe 40 to be mixed with contents of the second syringe 42 in the second syringe 42 prior to being introduced into the main chamber 18.

The first valve 32 can be any suitable one-way valve, device, or feature, within the first conduit 28, the second conduit 30, or at any other suitable position in the inlet housing 22 or the preparation device 10 generally that directs material inserted through the first inlet port 24 out through the second inlet port 26 along the first pathway D without entering the main chamber 18, and also directs material input through the second inlet port 26 into the main chamber 18 along the second pathway E without flowing to the first inlet port 24.

The second valve 34 is in the second conduit 30 between the first valve 32 and the main chamber 18. The second valve 34 is a one-way valve that permits flow of material through the second conduit 30 into the main chamber 18 and prevents flow of material within the main chamber 18 past the second valve 34. The second valve 34 can be any suitable one-way valve, device, or structural feature of the second conduit 30 and/or the inlet housing 22.

As illustrated in FIGS. 1 and 2, when the first inlet port 24 is not in use, it can be covered with a first cap 44 by connecting the first cap 44 to the first connector 36. When the second inlet port 26 is not in use, it can be covered with a second cap 46 by connecting the second cap 46 to the second connector 38. Thus, the first cap 44 is configured to mate with the first connector 36 and the second cap 46 is configured to mate with the second connector 38 using any suitable connection device or feature, such as a Luer fitting.

Figure 6:
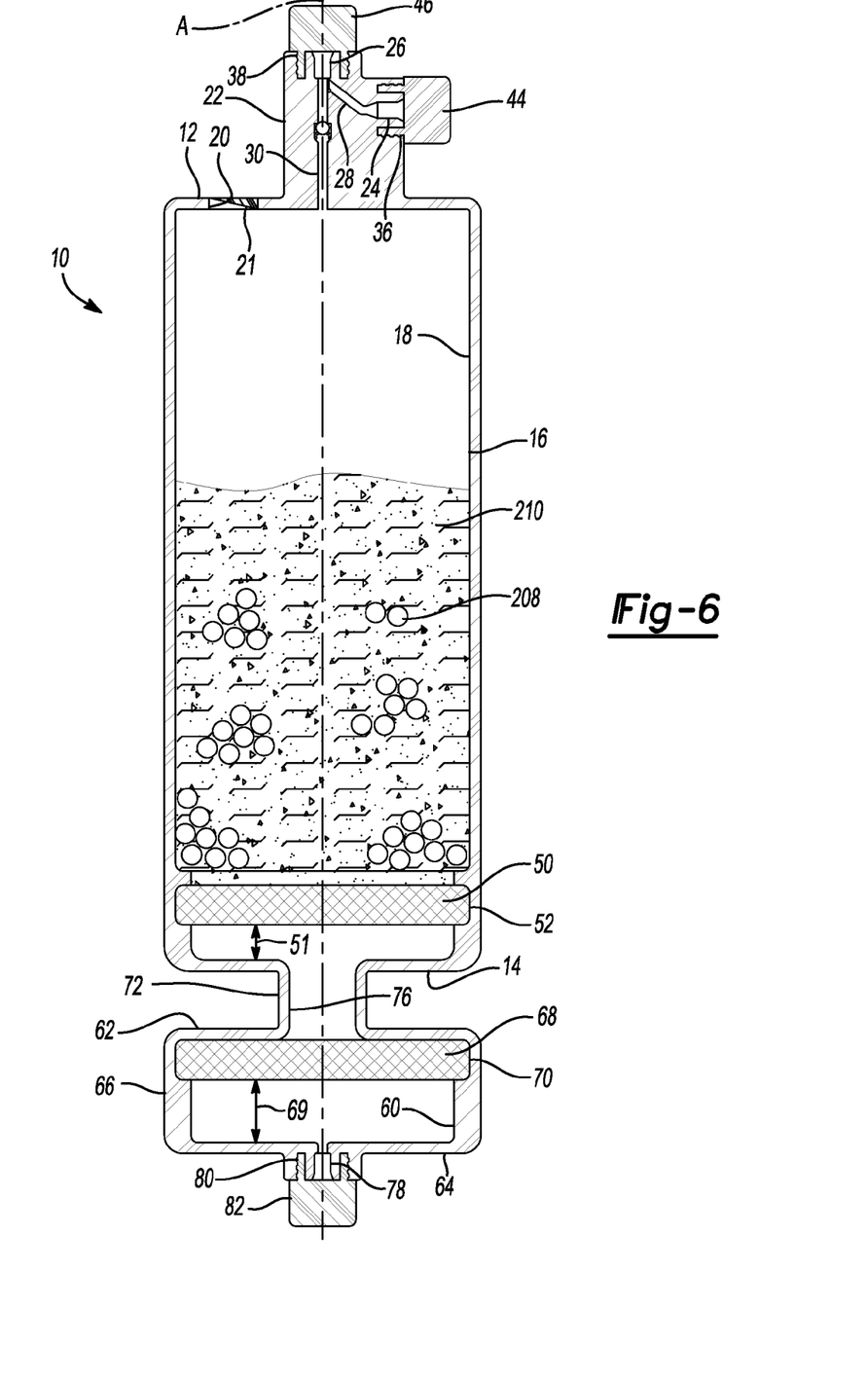
FIG. 6 is a cross-sectional view of the device of FIG. 1 through line 6-6 of FIG. 1 and illustrates material previously inserted within the main chamber of the device.

With reference to FIGS. 2 and 6, for example, the main chamber 18 includes a first filter 50. The first filter 50 is proximate to, but spaced apart from, the second end wall 14 and is seated within an annular recess 52 defined within an interior of the side wall 16. The first filter 50 and the second end wall 14 define a gap therebetween, which permits fluid to pass through an entirety of the first filter 50 into the gap. If the first filter 50 were seated flush against the second end wall 14, then flow of material through the first filter 50 would be restricted, for example, to the portion of the first filter 50 that extends across connection chamber 76 (described further below). The first filter 50 is generally a course filter that is configured to permit passage of clotting serum and restrict passage of other materials, including blood and plasma clots and activation materials, such as glass or desiccating beads and undissolved calcium. The first filter 50 can be any suitable type of filter or separation device configured to isolate clotting serum. For example, the first filter 50 can be a Plasmax® frit filter by Biomet of Warsaw, Ind., such as Part No. 800-0500-12 for example.

The preparation device 10 further includes a filter chamber 60. The filter chamber 60 is defined by a third end wall 62, a fourth end wall 64, and a side wall 66. The third end wall 62 is spaced apart from the fourth end wall 64 and thus the filter chamber 60 is spaced apart from the main chamber 18 and the first filter 50. The side wall 66 extends between the third end wall 62 and the fourth end wall 64. The third end wall 62 extends parallel to the fourth end wall 64. The side wall 66 is circular or cylindrical and defines the filter chamber 60 as a cylindrical chamber. The side wall 66 can also include multiple planar surfaces to define the filter chamber 60 as square or rectangular.

The filter chamber 60 includes a second filter 68, which is thus spaced apart from the first filter 50. The second filter 68 is mounted within the filter chamber 60 proximate to the main chamber 18 and spaced apart from the fourth end wall 64. The second filter 68 and the fourth end wall 64 define a second gap 69 therebetween. The second filter 68 is seated within a filter chamber annular recess 70. The filter chamber annular recess 70 is defined by an interior surface of the side wall 66. The second filter 68 is generally a fine, syringe filter that is configured permit passage of clotting serum and restrict passage of other materials, including blood and plasma clots and activation materials, such as glass or desiccating beads and undissolved calcium. The second filter 68 can be any suitable filter or separation device for isolating clotting serum, such as filter Part No. 01-20-0161 from Biomet of Warsaw, Ind. The second filter 68 can be mounted at any suitable position within the filter chamber 60 in addition to being proximate to the third end wall 62, as illustrated. The first filter 50 and the second filter 68 are optional and the preparation device 10 will function suitably without the first filter 50 and/or the second filter 68.

A connection portion 72 connects the filter chamber 60 to the main chamber 18. The connection portion 72 extends between the second end wall 14 of the main chamber 18 and the third end wall 62 of the filter chamber 60. The connection portion 72 includes a connection wall 74. The connection wall 74 defines a connection chamber 76, which provides fluid communication between the main chamber 18 and the filter chamber 60. The first longitudinal axis A extends through an axial center of the of the connection portion 72. The connection chamber 76 includes a smaller diameter than each of the main chamber 18 and the filter chamber 60. Thus, material drawn through the first filter 50 is first deposited in the first gap 51 and then pulled through the narrow connection portion 72 prior to being drawn through the second filter 68.

The filter chamber 60 further includes a first outlet port 78 aligned along the first longitudinal axis A. The first outlet port 78 can be any suitable opening, port, device, or feature that provides communication between the filter chamber 60 and an exterior of the preparation device 10. The first outlet port 78 can be provided at any suitable location to permit withdrawal of material out from within the preparation device 10. Proximate to the first outlet port 78 is a third connector 80, which is concentric with the first outlet port 78. The third connector 80 is a luer lock configured to cooperate with a withdrawal device (such as a syringe), another processing device (such as a mixing device, as described herein), or a third cap 82 to close the third connector 80 when not in use. The third connector 80 can be any suitable connection device or coupling device.

Figures 7A, 7B:
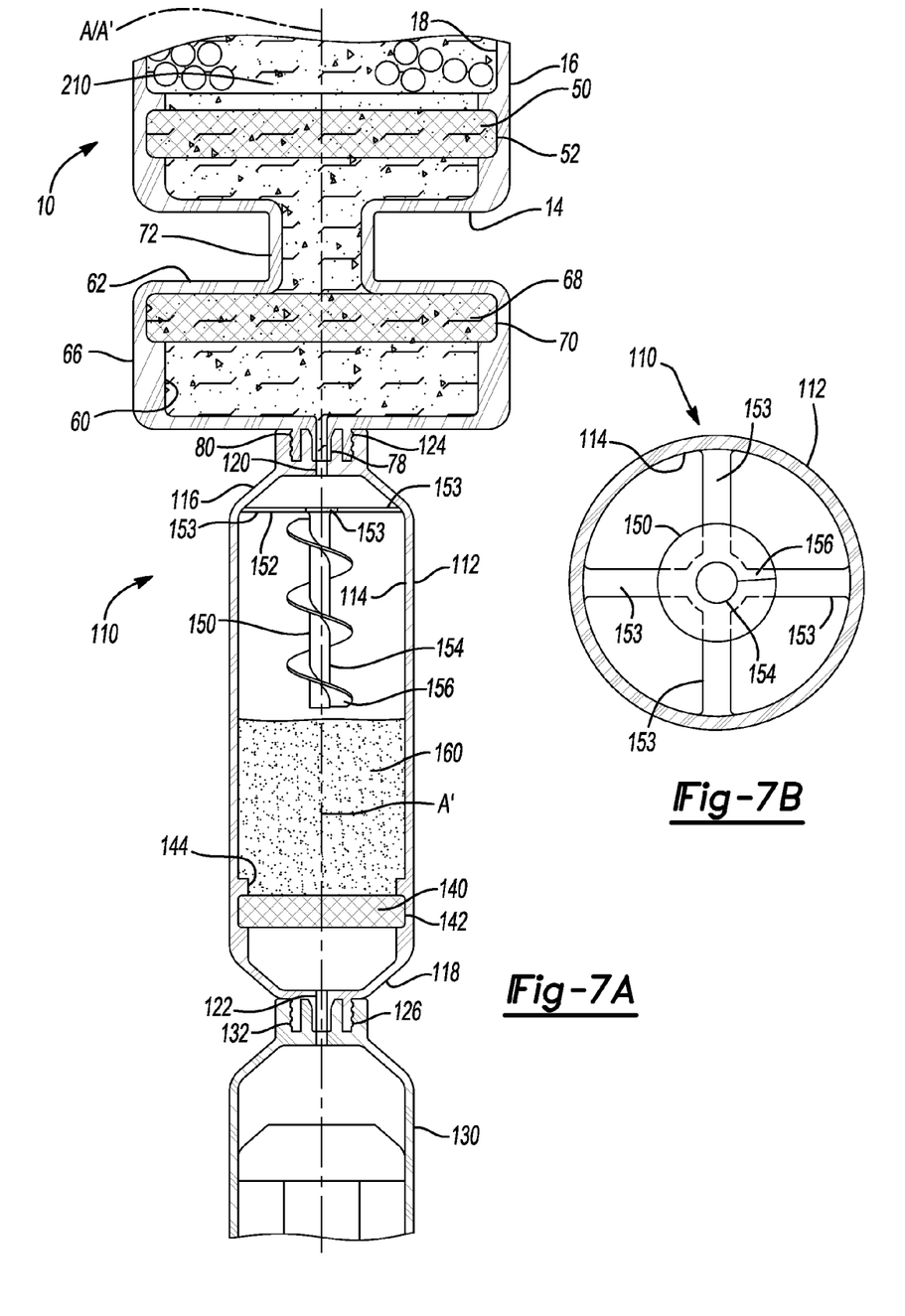
FIG. 7A is a cross-sectional view of a mixing device, a first end of the mixing device is connected to the preparation and isolation device of FIG. 1 and a second end of the mixing device is connected to a third syringe.
FIG. 7B is a bottom view of a disruptor of the mixing device of FIG. 7A.

With additional reference to FIGS. 7A and 7B, a mixing device is generally illustrated at reference numeral 110. The mixing device 110 generally includes a housing 112 that defines a reservoir 114. The housing 112 includes a first end 116 that is opposite to a second end 118. The housing 112 is tapered at the first end 116 and tapered at the second end 118. The housing 112 is cylindrical, and can be any other suitable shape as well.

A mixer inlet port 120 is at the first end 116 of the housing 102 and a mixer outlet port 122 is at the second end 118 of the housing 102. The mixer inlet port 120 is aligned with the mixer outlet port 122 along a mixing device longitudinal axis A' that extends through an axial center of the housing 112. The mixer inlet port 120 provides fluid communication between an exterior of the mixing device 110 and the reservoir 114 of the mixing device 110. The mixer outlet port 122 provides fluid communication between the reservoir 114 and an exterior of the mixing device 110. The mixer inlet port 120 and the mixer outlet port 122 can be at any other suitable location in the housing 102.

A fourth connector 124 is proximate to and concentric with the mixer inlet port 120. A fifth connector 126 is proximate to and concentric with the mixer outlet port 122. The fourth connector 124 can be any suitable connection device or connection feature configured to connect the mixing device 110 to the preparation device 10 at the first outlet port 78 of the preparation device 10 to provide fluid communication between the first outlet port 78 and the mixer inlet port 120. For example, the third connector 80 and the fourth connector 124 can each be luer lock connectors configured to mate with each another. The fifth connector 126 can be any suitable connection device or connection feature configured to connect the mixing device 110 to a clotting serum collection device. For example, the fifth connector 126 can be a luer lock connector configured to mate with a clotting serum collection syringe 130 including a syringe luer lock connector 132. The collection syringe 130 is configured to withdraw clotting serum out of the mixing device 110 through the mixer outlet port 122.

The mixing device 110 includes a third filter 140 within the reservoir 114 proximate to the second end 118 of the housing 112. The third filter 140 is seated in a third annular recess 142 that is defined at an inner surface 144 of the housing 112 and extends entirely around a circumference of the inner surface 144 of the housing 112. The third filter 140 can be secured within the housing 112 in any other suitable manner as well. The third filter 140 can be any suitable device configured to permit passage of clotting serum, while restricting passage of blood and plasma clots, undissolved calcium, and other activation materials within the mixing device 110. As further described herein, the third filter 140 is particularly useful in separating calcium added to clotting serum in the reservoir 114 that has not dissolved.

The housing 102 further includes a disruptor 150. The disruptor 150 includes a base 152, a post 154 extending from the base 152, and a spiral-sloped surface 156 mounted to the post 154. The spiral-sloped surface 156 extends around the post 154 and along a length of the post 154 in a step-wise manner. Both the spiral-sloped surface and the post 154 are fixed within the reservoir 114. The base 152 is mounted at the first end 116 of the housing 112 and the post 154 is orientated such that it extends along the mixing device longitudinal axis A'. The base 152 includes a plurality of support spokes 153 that support the base 152 at the first end 116, as illustrated in FIG. 7B. The support spokes 153 are spaced apart to permit flow of material therebetween and past the base 152. The disruptor 150 can include any suitable device, feature, or formation configured to disrupt flow of biological material flowing through the reservoir 114 and to thereby mix the biological material with other contents in the mixing device 110, including calcium as described herein. The disruptor 150 can be located at any other suitable location within the reservoir 114 and may be positioned in any other suitable orientation. Thus, as clotting serum or other material is drawn through the mixing device 110 it contacts the disruptor 150, which disrupts flow of the clotting serum and causes it to mix with other contents of the chamber, such as calcium.

The housing 102 further includes calcium 160 within the reservoir 104. The calcium 160 is between the disruptor 150 and the third filter 140. The calcium 160 can also be positioned at any other suitable location within the reservoir 104 and can be included in the third filter 140. The calcium 160 can include any suitable calcium, such as a solid calcium salt, including calcium chloride ($CaCl_2$). The calcium is dissolved into the clotting serum or other material as it passes through the third filter. Undissolved calcium is restricted from passing through the third filter 140.

With reference to FIGS. 3-8, use and operation of the preparation device 10 and the mixing device 110 to prepare and isolate clotting serum will now be described.

Clotting serum (including thrombin and various clotting factors) can be prepared from a variety of different sources, such as whole blood and plasma, each of which may be autologous or non-autologous. Any suitable type of plasma can be used, such as platelet rich plasma (PRP), platelet poor plasma (PPP), and concentrated platelet poor plasma. Plasma can be isolated using any suitable device or method. For example, PPP and PRP plasma can be isolated using the GPS® System by Biomet of Warsaw, Ind. Concentrated PPP can be prepared and isolated using the Plasmax® Plasma Concentration System by Biomet of Warsaw, Ind. Bone marrow plasma can be isolated using the MarrowStim™ Concentration System by Biomet of Warsaw, Ind.

When preparing clotting serum from whole blood, or any other material that includes red blood cells, the red blood cells are initially removed. For example, red blood cells are removed by placing whole blood in a test tube, GPS® System separation device, or any other suitable device, and centrifuged, such as for about 1-10 minutes, to separate the RBCs by density from other blood components. The RBCs are then removed with care using a syringe, or other suitable device, to ensure that the maximum amount of proteins are left in the blood. Any other suitable device and/or method for removing red blood cells from whole blood or any other suitable starting material can be used.

Preparation and isolation of clotting serum from whole blood will now be described. One skilled in the art will recognize that preparation and isolation of clotting serum from plasma or any other suitable clotting serum source or starting material will be similar.

Approximately 11 ml of whole blood with red blood cells removed is mixed with about 1 ml of Anticoagulant Citrate Dextrose Solution A (ACD-A) supplied by Citra Anticoagulants, Inc. and manufactured by Cytosol Laboratories, Inc., both of Braintree, Mass., or any other suitable anti-coagulant. The whole blood and anticoagulant can be mixed in a syringe by shaking. Any other suitable amount of whole blood and anticoagulant can be mixed in any suitable manner to prevent the whole blood from clotting.

The 12 ml of citrated blood is then mixed with a suitable clotting reagent, such as a reagent including ethyl alcohol and calcium chloride. A suitable reagent includes TPD™ Reagent by ThermoGenesis Corp. of Rancho Cordova, Calif. The citrated blood and reagent can be individually added to the main chamber 18 by, for example, coupling a citrated blood syringe to the second inlet port 26 and injecting the citrated blood into the main chamber 18; and separately coupling a reagent syringe to the second inlet port 26 and injecting the regent into the main chamber 18. The citrated blood and reagent are then mixed in the main chamber 18 of the preparation device 10.

Alternatively, the citrated blood and reagent can be mixed prior to being added to the main chamber 18. For example and with reference to FIGS. 3 and 4, TPD™ reagent 202 loaded in the first syringe 40 can be mixed in the second syringe 42 with 12 ml of citrated blood 204 loaded in the second syringe 42. The first syringe 40 loaded with the reagent 202 is connected to the inlet housing 22 at the first inlet port 24. A plunger 41 (FIG. 4) of the first syringe 40 is depressed to eject the reagent 202 from the first syringe 40 and into the first conduit 28 of the inlet housing 22. The reagent 202 moves along the first pathway D to contact the first valve 32 and cause the first valve 32 to move from the first position A to the second position B (FIG. 4). The reagent 202 is therefore free to pass from the first conduit 28 to the second conduit 30. Once in the second conduit 30, the reagent 202 flows out of the inlet housing 22, through the second inlet port 26, and into the second syringe 42 mounted to the second inlet port 26 at the second connector 38 as the reagent 202 continues along the first pathway D. With the first valve 32 in the second position B, the reagent 202 is restricted from flowing into the main chamber 18. After the reagent 202 passes across the first valve 32 and flow of the reagent 202 ceases, the first valve 32 returns to the first position A as a result of the first valve 32 being biased in the first position A (FIG. 5).

After the reagent 202 has been loaded into the second syringe 42 with the citrated blood 204, the second syringe 42 may be detached from the inlet housing 22 and shaken to mix the reagent 202 and citrated blood 204 together to provide a blood/reagent mixture 206. The second syringe 42 can be detached from the inlet housing 22 prior to being shaken or the second syringe 42 can be shaken while still attached to the inlet housing. As illustrated in FIG. 5, depressing a second plunger 43 of the second syringe 42 further mixes the reagent 202 and the citrated blood 204 and ejects the blood/reagent mixture 206 through the second inlet port 26, past the first valve 32 (which is in the first position A so as to not obstruct the second conduit 30), past the second valve 34, and into the main chamber 18. The second valve 34, which is a one-way valve, restricts the blood/reagent mixture 206 from exiting the main chamber 18 through the second inlet port 26. Once the blood/reagent mixture 206 is deposited in the main chamber 18, the first syringe 40 and the second syringe 42 are decoupled from the inlet housing 22 and the first and second inlet ports 24 and 26 are closed with the first and the second caps 44 and 46 respectively, in the manner described above.

Regardless of whether the reagent 202 and the citrated blood 204 are mixed before or after being introduced to the main chamber 18, an additional 0.015 g-0.04 g of calcium chloride reagent can be added to enhance clotting of the citrated blood 204. The additional calcium chloride can be added to the reagent 202 in the first syringe 40, to the citrated blood 204 in second syringe 42, or in the main chamber 18.

With additional reference to FIG. 6, the main chamber 18 includes glass beads 208 or any other suitable blood clotting activator, such as any type of desiccating beads, glass wool, titanium beads, etched glass, or titanium powder. The blood/reagent mixture 206 is mixed with the glass beads 208 for a suitable period of time until most, if not all, of the blood/reagent mixture 206 is brought to a foam. The blood/reagent mixture 206 is brought to a foam regardless of whether the reagent 202 and the citrated blood 204 are mixed before or after being introduced to the main chamber 18. This begins the conversion/activation of thrombin in the blood. The mixing can be done by vigorous hand shaking for 5 seconds to 30 seconds or more, or by any other suitable shaking device or method.

If the reagent 202 and the citrated blood 204 are mixed prior to being added to the main chamber 18, such as in the second syringe 42 as described above, the device 10 is left at room temperature and standard atmospheric pressure for about 25 minutes to allow the blood/reagent mixture 206 to clot and release clotting serum 210 into the main chamber 18, as illustrated in FIG. 6. The device 10 is laid on a flat surface such that the longitudinal axis A is parallel to the surface and the glass beads 208 are evenly distributed throughout the chamber to enhance clotting throughout the blood/reagent mixture 206 by maximizing the amount of the blood/reagent mixture 206 in contact with the glass beads 208. It is not necessary to subject the device 10 to a vacuum when the reagent 202 and the citrated blood 204 are mixed prior to being added to the main chamber 18, which thus facilitates use of the device 10 in the operating room to prepare and isolate clotting serum.

If the reagent 202 and the citrated blood 204 are not mixed prior to being added to the main chamber 18, instead of being left at room temperature and standard atmosphere for about 25 minutes, the device 10 is placed under a vacuum for about 5 minutes to about 30 minutes or more to increase foaming and accelerate clotting, which results in release of the clotting serum 210. The device 10 is positioned in the vacuum chamber by laying the device 10 on its side so that the longitudinal axis A is parallel to a base of the vacuum chamber, the vacuum port 20 is furthest away from the base of the vacuum chamber, and the glass beads 208 are evenly distributed throughout the main chamber 18 of the preparation device 10. At the end of the vacuum cycle, the device 10 is inverted several times to disperse the glass beads 208 throughout the main chamber 18.

Mixing the reagent 202 and the citrated blood 204 before insertion in the main chamber 18 is desirable because doing so eliminates the need for a vacuum. But regardless of whether the reagent 202 and the citrated blood 204 are mixed before or after being inserted in the main chamber 18, the contents of the main chamber 18 need not be heated, which expedites clotting and results in the clotting serum 210 being released more quickly.

Figure 8:
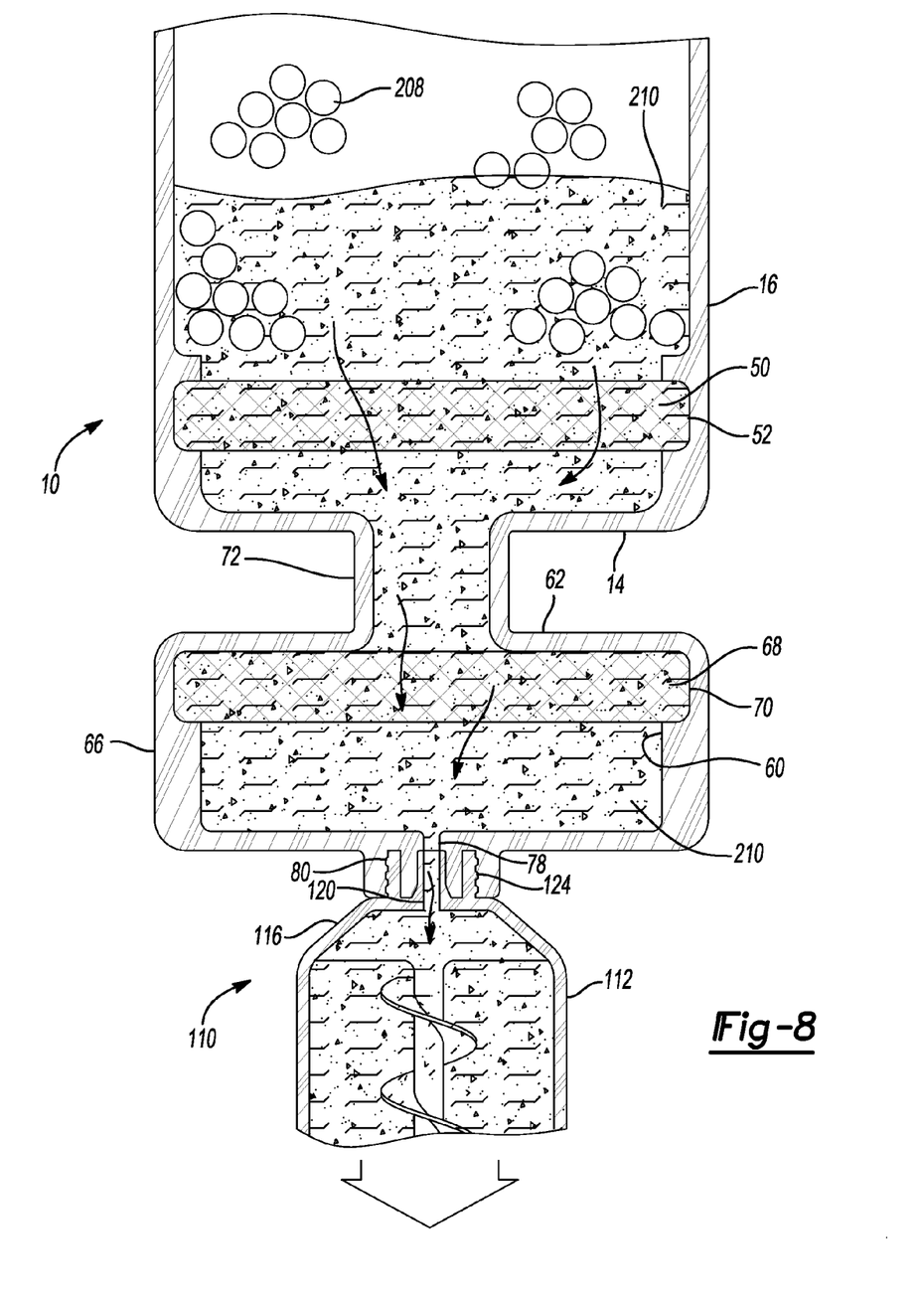
FIG. 8 is a cross-sectional view of the preparation and isolation device of FIG. 1 connected to the mixing device of FIGS. 7A and 7B and material being extracted from the preparation and isolation device through the mixing device.

After the clotting serum 210 has been released from the blood/reagent mixture 206 into the main chamber 18, the clotting serum 210 is isolated from the glass beads 208, the clotted blood, any undissolved calcium, and the rest of the contents of the main chamber 18. With reference to FIGS. 7 and 8, the clotting serum 210 is isolated by drawing the clotting serum 210 through both the first filter 50 and the second filter 68, and ultimately out of the device 10 through the first outlet port 78 using the clotting serum collection syringe 130, or any other suitable extraction device or method. Because the first filter 50 and the second filter 68 are sized to permit passage of the clotting serum 210, but restrict passage of the glass beads 208, clotted blood, and undissolved calcium, the first filter 50 and the second filter 68 isolate the clotting serum 210 from the other contents of the main chamber 18. Further, because the clotting serum 210 is pulled through the clotted blood, the clotting serum 210 can include additional clotting factors.

If the device 10 does not include the first filter 50 and/or the second filter 68, the clotting serum 210 can be separated from the other contents of the main chamber 18 by centrifuging the device 10 for a suitable amount of time at a suitable speed, such as from about 30 seconds to about 5 minutes at about 3,200 RPM. The device 10 can be provided with an outlet tube (not shown) extending from the first outlet port 78 to an area in the main chamber 18 where the clotting serum 210 is known to settle after centrifugation, which will depend on the area of the main chamber 18, as well as the amount of both the reagent 202 and the citrated blood 204 introduced into the main chamber 18, as one skilled in the art will recognize. The clotting serum 210 can be extracted through the first outlet port 78 using any suitable method or device, such as the serum collection syringe 130.

Additional calcium can be added to the clotting serum 210 to increase its effectiveness as a clotting agent. Various forms of calcium can be added, including calcium salts, such as calcium chloride. The calcium can be added in any suitable manner. For example, calcium salt can be added to the fraction of glass beads 208 in the main chamber 18 and/or calcium salt can be included in the collection syringe 130.

Calcium salt can also be deposited on the first filter 50 and the second filter 68 of the device 10 by exposing surfaces of the first and second filters 50 and 68 to an aqueous calcium salt solution and then removing the water thereby depositing calcium salt on the surfaces of each of the first filter 50 and the second filter 68. Upon subsequent extraction of the clotting serum 210 out of the main chamber 18 through the first and the second filters 50 and 68, the calcium salts dissolve and increase the calcium concentration of the clotting serum 210.

With reference to FIG. 7, additional calcium 160 can be included in the mixing device 110 mounted to the preparation device 10 at the first outlet port 78. The calcium 160 can include a suitable calcium salt, such as calcium chloride. The calcium 160 can be provided in loose powder form or be dried onto a surface of the reservoir 114 as a solid. The collection syringe 130 is mounted to the mixer outlet port 122 to draw the clotting serum 210 through the reservoir 114 of the mixing device. As the clotting serum 210 is drawn into the reservoir 114 through the mixer inlet port 120 and the openings 153 of the base 152, and then subsequently through the reservoir 114, flow of the clotting serum 210 is disrupted as it contacts the disruptor 150, which causes the clotting serum 210 to mix with the calcium 160 and dissolve the calcium salt to increase the calcium concentration of the clotting serum 210. The clotting serum 210 with increased calcium concentration is pulled through the third filter 140, which restricts passage of particulate or unsolubilized calcium salt. Finally, the clotting serum 210 is extracted from the mixing device 110 and into the collection syringe 130.

The extracted clotting serum can be used for any suitable therapeutic purpose. For example, the clotting serum can be used to clot blood, PRP, PPP and concentrated PPP in a timely and efficient manner. The blood, PRP, PPP, and concentrated PPP can be from autologous or nonautologous sources and can be prepared and isolated using a variety of different methods and devices, such as the GPS®, Plasmax®, or MarrowStim™, all by Biomet of Warsaw, Ind. The clotting serum includes clotting factors that rapidly convert, for example, GPS® platelet concentrate into platelet gel and PPP; and convert Plasmax® fibrinogen to fibrin. The platelet gel is useful in various clinical applications, including the promotion of hemostasis and acceleration of vascularization following a surgical intervention.

The clotting serum can be mixed with blood, PRP, PPP, and concentrated PPP in any suitable ratio to induce clotting, such as: 1 ml-2 ml of clotting serum with 1 ml-2 ml of blood PPP, PRP, or concentrated PPP; 0.5 ML of clotting serum to 1 ml of blood, PPP, PRP, or concentrated PPP; or 1 ml of clotting serum to 10 ml of blood, PPP, PRP, or concentrated PPP.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A clotting serum production device comprising:
   a main chamber;
   an inlet assembly comprising a first inlet port, a second inlet port, a first conduit, and a second conduit, wherein the first conduit comprises a first one-way valve configured to be movable between a first position and a second position, the first position restricting fluid flow from the first conduit to the second inlet port and permitting fluid flow from the second inlet port to the main chamber, and the second position directing fluid flow from the first conduit to the second inlet port and restricting fluid flow from the second inlet port to the main chamber; and
   an outlet port in fluid communication with the main chamber.

2. The device of claim 1, further comprising:
   a first filter mounted within the main chamber; and
   a second filter spaced apart from the main chamber and connected to the main chamber by a connection portion.

3. The device of claim 1, wherein the main chamber defines a longitudinal axis, and the second inlet port and the outlet port are aligned with the longitudinal axis.

4. The device of claim 1, wherein the main chamber includes a vacuum port configured to permit air flow out of the main chamber and to restrict air flow into the main chamber.

5. The device of claim 1, the inlet assembly further comprising a second one-way valve disposed in the second conduit between the main chamber and a junction of the second conduit and the first one-way valve.

6. The device of claim 1, the inlet assembly further comprising a second one-way valve disposed along the second conduit, the one-way valve configured to permit fluid flow into the main chamber and restrict fluid flow from the main chamber into the second conduit.

7. The device of claim 1, further comprising a filter in fluid communication with the main chamber, wherein the filter includes calcium.

8. The device of claim 1, wherein the first conduit connects to the second conduit at an angle greater than 90° as measured between an axis of the first conduit and an axis of the second conduit.

9. The device of claim 1, further comprising a filter chamber, wherein a connection portion between the main chamber and the filter chamber has a smaller diameter than a diameter of the main chamber and a diameter of the filter chamber.

10. The device of claim 1, further comprising a filter disposed within the main chamber and spaced apart from the second end wall to define a gap between the filter and the second end wall.

11. The device of claim 1, further comprising a filter chamber in fluid communication with the main chamber, wherein the outlet port is provided in an end wall of the filter chamber.

12. The device of claim 11, wherein a filter of the filter chamber is spaced apart from the end wall of the filter chamber to define a gap between the filter and the end wall of the filter chamber.

13. The device of claim 1, further comprising a mixing device mounted to the outlet port, the mixing device including calcium.

14. The device of claim 1, wherein the first inlet port is disposed at about 90° relative to the second inlet port, and the second inlet port is aligned with a longitudinal axis of the main chamber.

15. A clotting serum production device comprising:
a main chamber comprising a filter having a deposit of a dried calcium salt, the filter configured to supply calcium to a fluid flowing through the main chamber and to permit passage of the fluid and to restrict passage of blood clots, plasma clots, glass beads, or desiccating beads;
a first inlet port in communication with a first conduit, and a second inlet port in communication with a second conduit, the second conduit extending from the second inlet port to the main chamber, wherein the first conduit is configured to direct one-way fluid communication from the first inlet port to the second inlet port, and the second conduit is configured to provide one-way fluid communication from the second inlet port to the main chamber; and
an outlet port in fluid communication with the main chamber.

16. The device of claim 15, wherein the first conduit comprises a one-way valve moveable between a first position and a second position, the first position restricting fluid communication between the first conduit to the second conduit while permitting fluid communication from the second inlet port to the main chamber, and the second position permitting fluid communication from the first conduit to the second conduit while restricting fluid communication from the second inlet port to the main chamber.

17. The device of claim 16, wherein the one-way valve comprises a flap valve or a hinge valve.

18. A clotting serum production device comprising:
a main chamber comprising a one-way valve, the one-way valve configured to permit air flow out of the main chamber, to restrict air flow into the main chamber, and to restrict fluid flow into and out of the main chamber;
an inlet assembly extending from the main chamber, the inlet assembly comprising a first inlet port, a second inlet port, a first conduit extending between the first inlet port and a second conduit, the second conduit extending from the second inlet port to the main chamber, wherein the inlet assembly includes of a first valve configured to direct one-way fluid flow from the first inlet port to the second inlet port and a second valve configured to provide one-way fluid flow from the second inlet port to the main chamber; and
an outlet port in fluid communication with the main chamber that provides fluid communication with an exterior of the clotting serum production device.

19. The device of claim 18, wherein the first valve is moveable between a first position and a second position, wherein in the first position the first valve restricts fluid flow of material from the first conduit to the second inlet port and permits fluid flow from the second inlet port to the main chamber, and in the second position the first valve fluid flow from the first conduit to the second inlet port and restricts fluid flow from the second inlet port to the main chamber.

20. The device of claim 18, wherein the first conduit connects to the second conduit at an angle greater than 90° as measured between an axis of the first conduit and an axis of the second conduit.

* * * * *